(12) United States Patent
Lin et al.

(10) Patent No.: US 8,734,343 B2
(45) Date of Patent: May 27, 2014

(54) REAL-TIME PHYSIOLOGICAL SIGNAL MEASUREMENT AND FEEDBACK SYSTEM

(75) Inventors: Yuan-Hsiang Lin, Taipei (TW); Chih-Fong Lin, Taipei (TW); He-Zhong You, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 0 days.

(21) Appl. No.: 13/584,880

(22) Filed: Aug. 14, 2012

(65) Prior Publication Data

US 2013/0085346 A1 Apr. 4, 2013

(30) Foreign Application Priority Data

Oct. 4, 2011 (TW) .............................. 100135894 A

(51) Int. Cl.
*A61B 5/00* (2006.01)
*G06F 19/00* (2011.01)

(52) U.S. Cl.
CPC ............... *G06F 19/34* (2013.01); *A61B 5/6816* (2013.01); *A61B 5/683* (2013.01); *A61B 2562/14* (2013.01)
USPC .......................................... 600/300; 600/323

(58) Field of Classification Search
USPC .................... 600/300–301, 323, 324
See application file for complete search history.

(56) References Cited

U.S. PATENT DOCUMENTS

| | | | |
|---|---|---|---|
| 8,532,729 B2 * | 9/2013 | Medina et al. ................. 600/344 |
| 2004/0152957 A1 * | 8/2004 | Stivoric et al. ................ 600/300 |
| 2007/0299325 A1 * | 12/2007 | Farrell et al. .................. 600/301 |
| 2008/0109041 A1 * | 5/2008 | de Voir ............................... 607/7 |
| 2008/0146892 A1 * | 6/2008 | LeBoeuf et al. ............... 600/300 |
| 2009/0099425 A1 * | 4/2009 | Starr et al. ..................... 600/301 |
| 2010/0094502 A1 * | 4/2010 | Ito et al. ........................... 701/36 |
| 2010/0217099 A1 * | 8/2010 | LeBoeuf et al. ............... 600/301 |
| 2010/0217103 A1 * | 8/2010 | Abdul-Hafiz et al. ........ 600/322 |
| 2010/0292585 A1 * | 11/2010 | Uenishi et al. ................. 600/486 |
| 2011/0098112 A1 * | 4/2011 | LeBoeuf et al. ................. 463/31 |
| 2011/0106627 A1 * | 5/2011 | LeBoeuf et al. ........... 705/14.66 |
| 2011/0295081 A1 * | 12/2011 | Tatara et al. ................... 600/300 |
| 2011/0295092 A1 * | 12/2011 | Tatara et al. ................... 600/310 |
| 2012/0130203 A1 * | 5/2012 | Stergiou et al. ............... 600/301 |
| 2012/0253152 A1 * | 10/2012 | Haisley et al. ................. 600/323 |

* cited by examiner

*Primary Examiner* — Bill Thomson
*Assistant Examiner* — Bobby Soriano
(74) *Attorney, Agent, or Firm* — Bacon & Thomas, PLLC

(57) ABSTRACT

A real-time physiological signal measurement and feedback system is suitable to be worn on a body part of an user for decreasing the noise of motion, and includes a sensor module, a signal processing module and a feedback platform. The sensor module includes a first magnetic unit having a light emitting diode and a second magnetic unit having a photo-detector. The light emitting diode illuminates a light beam passing through the body part and being received by the photo-detector so as to generate an electric signal when both of the first and the second magnetic units attract mutually to sandwich the body part. The signal processing module converts the electrical signal into a digital signal. The feedback platform processes the digital signal to generate a physiological parameter, and is used as a multi-function driving recorder. An alarm is triggered or not by the feedback platform according to the physiological parameter.

11 Claims, 8 Drawing Sheets

REAL-TIME PHYSIOLOGICAL SIGNAL MEASUREMENT AND FEEDBACK SYSTEM

BACKGROUND OF THE INVENTION (1) Field of the Invention

The invention relates to an physiological signal measurement system, and especially relates to a signal measurement and feedback system for real-time photoplethysmograph.

(2) Description of the Prior Art

Generally speaking, for the purpose of measuring physiological signal such as photoplethysmograph, two conventional sensing methods are popularly adopted: fingertip clip sensor module and finger ring sensor module. A typical fingertip clip sensor module mainly comprises a pair of shanks, which are crisscross pivotal jointed in respective middle section in scissors-like manner such that each shank serves as a prong of an integrated fingertip clip sensor module. Each shank includes a front jaw and a rear levering stem in addition to the middle pivotal section, which acts as a fulcrum at the pivotal joint. One front jaw of a shank contains a light-emitting diode (LED) while the other front jaw of another shank contains light sensing receiver such as photocell, photodiode or the like so that the pair of front jaws forms a sensor module. The pair of rear levering stems are lightly spring-propped so that the pair front jaws remain in close status if in idle mode while the pair front jaws can be opened and comfortably clip a finger of the examinee in loosely clamping manner without any painful pinch feeling in operation mode. In this operation mode, the front jaw with light-emitting diode (LED) will illuminate light beam to pass through the finger of the examinee to reach the other front jaw with light sensing receiver, which perceives brightness fluctuation of received light beam in conformity with variance of the blood content in the finger.

The typical fingertip clip sensor module can be further adapted into various shapes, but all of them have common easily drop off drawback. Because the fingertip clip sensor module can only loosely clamp the finger of the examinee to assure a comfortably clip without any painful pinch feeling in operation mode, it is easily dropped off due to inadvertently pull and drag or sudden movement of the examinee. To overcome foregoing drawback of the fingertip clip sensor module, the finger ring sensor module is introduced into measurement of the physiological signal such as photoplethysmograph. The finger ring sensor module comprises a ring-shaped holder, which includes a light-emitting diode (LED) and a light sensing receiver such as photocell, photodiode or the like respectively juxtaposed in opposed sides therein, so that the finger ring holder is used as an integral sensor module. In practical usage, the examinee just snugly wears the finger ring holder of the finger ring sensor module onto the finger, the light-emitting diode (LED) therein will illuminate light beam to pass through the finger of the examinee to reach the light sensing, receiver therein, which perceives brightness fluctuation of received light beam in conformity with variance of the blood content in the finger. Though the finger ring sensor module solves the easily drop off drawback of the fingertip clip sensor module, but it creates another drawback that no universal ring size can meet various finger dimensions of different examinees. Besides, the perceived brightness fluctuation from either fingertip clip sensor module or finger ring sensor module can be further well conditioned by a suite of measuring devices and relayed to display in related medical monitor in combination as a meaningful physiological signal. Thus, by means of foregoing operation, the fingertip clip sensor module and finger ring sensor module can be used to acquire suitable physiological signal such as photoplethysmograph of the examinee to be interpreted by medical personnel for diagnostic and pathological usage.

However, the foregoing suite of measuring devices and medical monitor for conditioning the perceived brightness fluctuation form the fingertip clip sensor module and finger ring sensor module is always bulky and complicated in association, which confines the application being limited in clinical usage and cumbersome unable for daily living usage outside of clinics. To solve issue mentioned above, a light and portable headphone sensor module is invented. For example, a patent title of "Measuring headphone of heart rate variability" in Taiwan Patent No. 201036591 contrives the measuring headphone containing a sensor module with a light-emitting diode (LED) and a light sensing receiver such as photocell, photodiode or the like embedded therein. In practical usage, the examinee just snugly wears the measuring headphone containing the sensor module onto the head, the light-emitting diode (LED) therein will illuminate light beam to reflect from the auricular blood of the examinee to backwardly reach the light sensing receiver therein, which perceives brightness fluctuation of received light beam in conformity with variance of the blood content in the finger. In this optical aspect of reflecting light beam from the auricular blood, time headphone sensor module is classified as reflective sensor module category while both of the fingertip clip sensor module and finger ring sensor module, which apply the same optical principle in passing light beam through finger, are classified as transmissive sensor module category. For sensitivity comparison, the brightness fluctuation signal of the reflective sensor module category is much weaker than that of the transmissive sensor module category so that the reflective sensor module category is much more vulnerably affected by the noise interference such as motion artifact than the transmissive sensor module category.

In conclusion, the drawbacks of foregoing conventional sensor modules are summarized as below. For fingertip clip sensor module, it has easily dropping off drawback and cumbersome drawback in associated suite of measuring devices and medical monitor. For fingertip ring sensor module, it has drawback in no universal ring size able to meet various finger dimensions of different examinees in addition of cumbersome drawback in associated suite of measuring devices and medical monitor. For headphone sensor module, it has drawback in being vulnerably affected by the noise interference of motion artifact. Therefore, how to simultaneously solve all the drawbacks of three foregoing conventional sensor modules of physiological signal having features of high functional usage with obviation of noise interference and low power consumption during practical operation becomes an urgent problem in the technical field of the present invention.

SUMMARY OF THE INVENTION

One object of the invention is to provide a real-time physiological signal measurement and feedback system. The system has a sensor module which can be securely worn by a user via the magnetic units. In addition, the sensor module can effectively decrease the noise interference when sensing the physiological signal of the motion user.

Another object of the invention is to provide a feedback platform. The feedback platform is used to provide an alarm for the user if any abnormality of received physiological parameter is detected, and serves to relay both of the physiological parameter and the position of the user to the medical personnel for judging how to handle it.

In one aspect, the invention provides a real-time physiological signal measurement and feedback system comprising a sensor module, a signal processing module and a feedback platform.

The sensor module is adapted to being held on a body part of an user, and comprises a first magnetic unit with a light emitting diode (LED) and a second magnetic unit with a photo-detector. The light emitting diode illuminates a light beam passing through the body part of the user and being received by the photo-detector thereby a first electric signal is generated by the photo-detector when the first magnetic unit and the second magnetic unit magnetically attract mutually and sandwich the body part of the user therebetween. In an embodiment, the sensor module comprises a gravity sensing element so that the gravity sensing element generates a third electric signal if the sensor module is shaken.

The signal processing module is electrically connected to the sensor module for receiving the first electric signal therefrom, and comprises an operation amplifier, a converter and a wireless transmitter. The operation amplifier is used for processing the first electric signal to output a second electric signal. The converter is electrically connected to the operation amplifier for receiving the second electric signal therefrom, and converts the second electric signal into a digital signal. The wireless transmitter is electrically connected to the converter for sending the digital signal to the signal processing module.

The feedback platform comprises a wireless receiver, a real-time process unit and an alarm unit. The wireless receiver is used to receive the digital signal from the wireless transmitter. The real-time process unit is signally connected to the wireless receiver for generating the physiological parameter according to the digital signal. The alarm unit is electrically connected to the real-time process unit for triggering the alarm.

In an embodiment, the digital signal includes a noise, so that the real-time process unit comprises a bandpass filter, a squaring amplifier and a differential amplifier. The bandpass filter is used to remove the noise from the digital signal. The squaring amplifier is used to amplify the digital signal after the noise is removed from precedent bandpass filter. The differential amplifier is used to differentiate the digital signal amplified by the squaring amplifier for extracting a slope value. The real-time process unit further comprises a wave peak detector and a heart rate counter. The wave peak detector is used to obtain a plurality of wave peak values in accordance with the slope value. The heart rate counter is used to obtain a heart rate value (HR) in accordance with a time interval between two wave peak values.

In an embodiment, the alarm unit comprises a referential threshold range for triggering the alarm if the physiological parameter exceeds the referential threshold range. The alarm is a sound alerting effect, a vibration alerting effect or a visual alerting message prompt.

In an embodiment, the feedback platform comprises a mobile communication device and is signally connected to a supervisory platform comprising a medical center. The feedback platform comprises a positioning system and a vehicle driving recording system. The positioning system is used for getting a position of the user. The vehicle driving recording system records a driving video; and the feedback platform is used to transmit the physiological parameter and the position of the user as well as the driving video to the supervisory platform. The driving video includes an image inside and outside the vehicle.

In an embodiment, besides generating the physiological parameter, the feedback platform is a multi-function driving recorder for generating an image data, and recording the image data and the physiological parameter.

Compared with the prior arts, the embodiments of the present invention modify the structure of the sensing module in the real-time physiological signal measurement and feedback system. By means of two magnetic units securely fixing on a part of human body of the user, the sensor module of the present invention can significantly reduce noises, so as to improve the quality of the original signal. The sensor module can easily fix on the earlobe of the user, like a Bluetooth earphone, but not affect daily activities.

Other objectives, features and advantages of the present invention will be further understood from the further technological features disclosed by the embodiments of the present invention wherein there are shown and described preferred embodiments of this invention, simply by way of illustration of modes best suited to carry out the invention.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. In this regard, directional terminology, such as "top," "bottom," "front," "back," etc., is used with reference to the orientation of the Figure(s) being described. The components of the present invention can be positioned in a number of different orientations. As such the directional terminology is used for purposes of illustration and is in no way limiting. On the other hand, the drawings are only schematic and the sizes of components may be exaggerated for clarity. It is to be understood that other embodiments may be utilized and structural changes may be made without departing from the scope of the present invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. Similarly, the terms "facing," "faces" and variations thereof herein are used broadly and encompass direct and indirect facing, and "adjacent to" and is variations thereof herein are used broadly and encompass directly and indirectly "adjacent to". Therefore, the description of "A" component facing "B" component herein may contain the situations that "A" component facing "B" component directly or one or more additional components is between "A" component and "B" component. Also, the description of "A" component "adjacent to" "B" component herein may contain the situations that "A" component is directly "adjacent to" "B" component or one or more additional components is between "A" component and "B" component. Accordingly, the drawings and descriptions will be regarded as illustrative in nature and not as restrictive.

Figure 1:
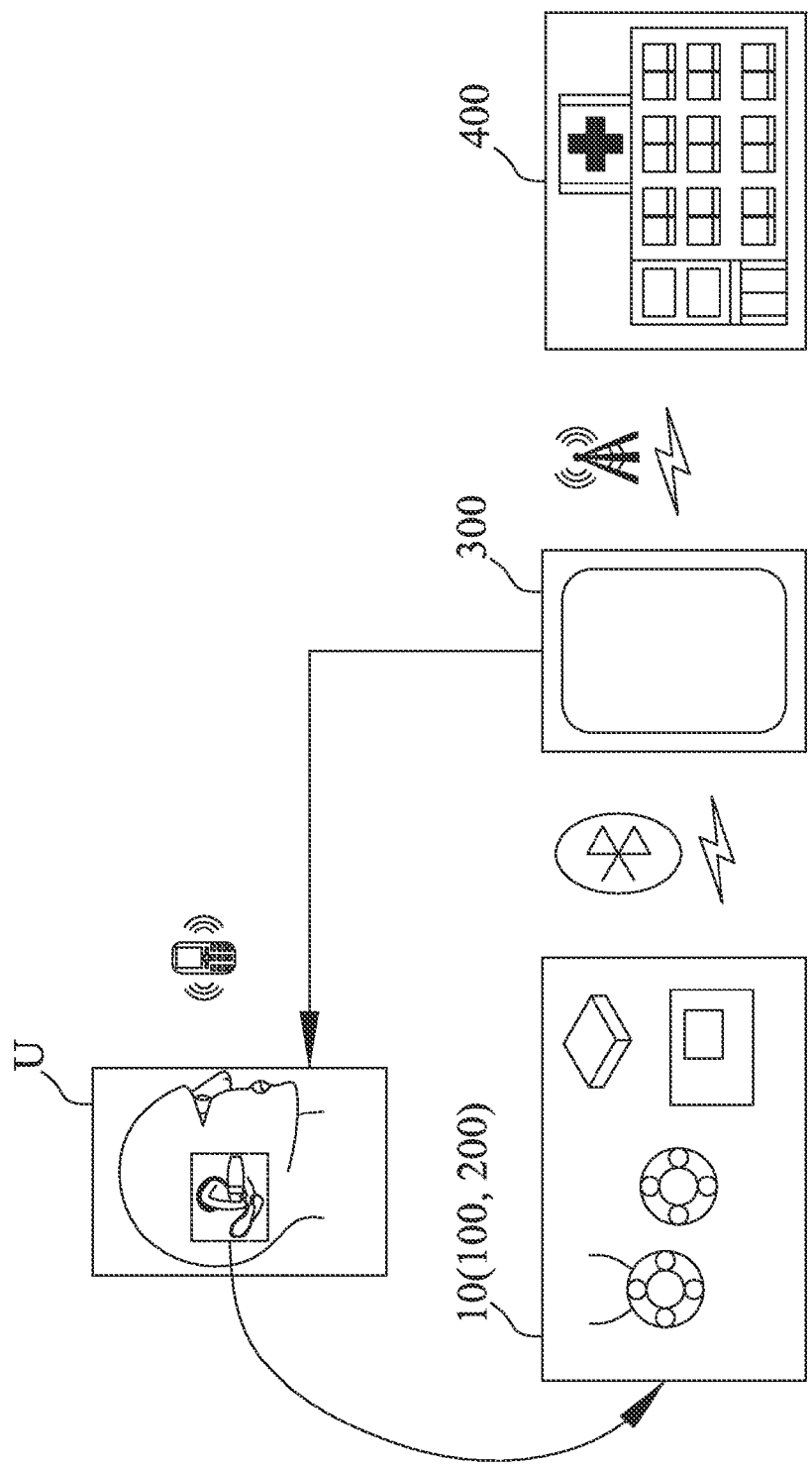
FIG. 1 is a schematic block diagram for a real-time physiological signal measurement and feedback system in a preferred exemplary embodiment of the present invention.

Please refer to FIG. 1, which is a schematic block diagram in an exemplary embodiment of the present invention for a real-time physiological signal measurement and feedback system that is suitable for an examinee user U to firmly wear on a part of human body such as earlobe for effectively decreasing the noise interference of motion artifact. The system comprises a sensor module 100, a signal processing module 200 and a feedback platform 300 such that both of the sensor module 100 and signal processing module 200 are preferably embedded in an earphone 10. The earphone 10, which is also called headset or headphone in some cases and preferably a subsidiary of a smart phone, serves to be securely held on the auricle of the examinee user U for convenient wear. The sensor module 100 is used for perceiving and acquiring external signal. The signal processing module 200 is used to extract, condition and process signals from the sensor module 100. The feedback platform 300 is used to record and transmit the signals from signal processing module 200 into a remote supervisory platform 400 of a medical center for being interpreted by the medical personnel, who can also timely alert the examinee user U.

Figure 2:
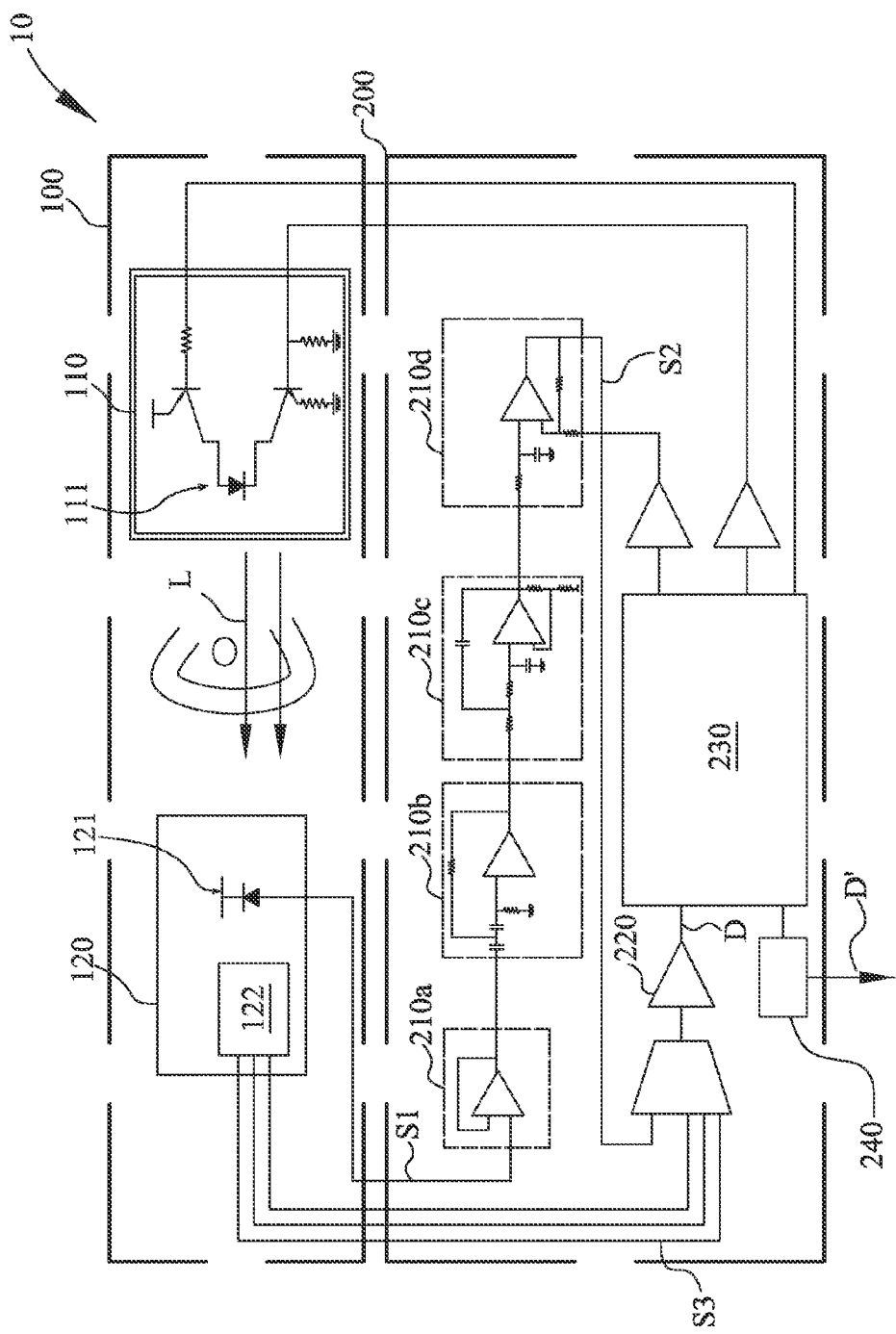
FIG. 2 is a schematic block diagram showing the PPG sensor module and signal processing module in a preferred exemplary embodiment of the present invention.

Please refer to FIG. 2, which is a schematic block diagram showing the sensor module 100 and signal processing module 200 in an exemplary embodiment of the present invention. The sensor module 100 includes a first magnetic unit 110 with a light emitting diode (LED) 111 and a second magnetic unit 120 with a photo-detector 121 such that the light emitting diode 111 illuminates a light beam L passing through a body part of the examinee user U and being received by the photo-detector 121 thereby a first electric signal S1 is generated by the photo-detector 121 when the first magnetic unit 110 and the second magnetic unit 120 magnetically attract mutually and sandwich the body part of the examinee user U therebetween.

Figure 3:
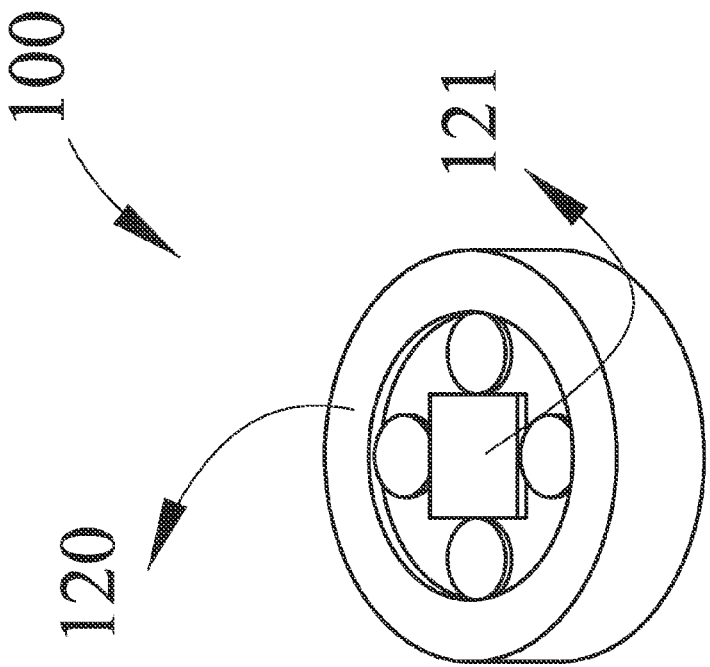
FIG. 3 is a structural view showing the optical sensors and magnetic rings of the PPG sensor module in a preferred exemplary embodiment of the present invention.
Figure 3:
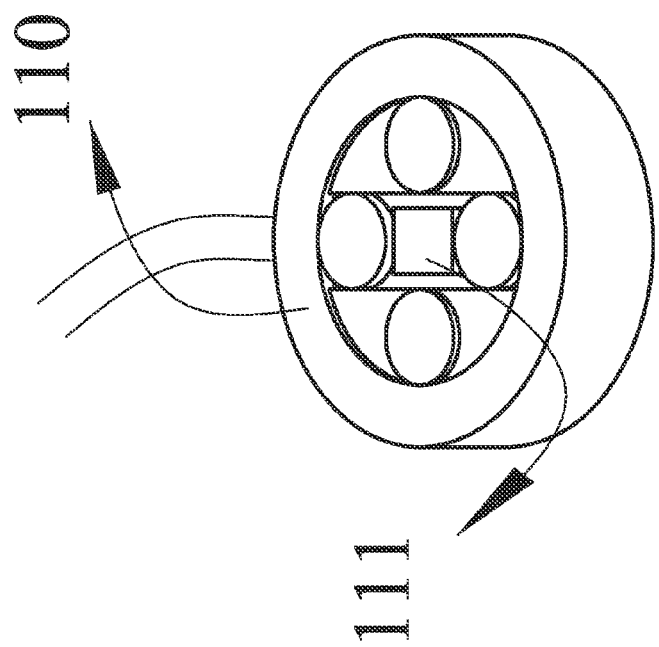

Please refer to FIG. 3, which is a structural view showing the optical sensors and magnetic rings of the sensor module 100 in an exemplary embodiment of the present invention. Each peripheral of the first magnetic unit 110 and the second magnetic unit 120 is formed in ring shape and made of neodymium magnet with strong permanent magnetic force in composition of neodymium, iron and boron. The light emitting diode 111 is enclosed in the first magnetic unit 110 while the photo-detector 121 is enclosed in the second magnetic unit 120 such that the light emitting diode 111 is preferably an infrared light emitting diode (IR LED).

In practical usage, when the examinee user U wears the sensor module 100 on a earlobe by sandwiching, his/her earlobe between the first magnetic unit 110 and the second magnetic unit 120, both of the light emitting diode 111 in the first magnetic unit 110 and the photo-detector 121 in the second magnetic unit 120 will immediately align each other via the magnetically attract mutually between both magnetic ring peripherals of the first magnetic unit 110 and the second magnetic unit 120 so that the earlobe of the examinee user U is securely clipped by the sensor module 100. Thereby, the contrivance of the sensor module 100 enables the real-time physiological signal measurement and feedback system of the present invention to be used in daily living activities in stable manner with reducing motion artifacts so that rest body parts of the examinee user U are free in movement without causing any interference noise.

The signal processing module 200, which is electrically connected to the sensor module 100 for receiving the first electric signal S1 therefrom, includes a set of operation amplifiers (OP) 210a-210d, a converter 220, a microprocessor 230 and a wireless transmitter 240. The set of operation amplifiers 210a-210d, which includes a buffer 210a, high-pass filter 210b, low-pass filter 210c and an automatic gain controller (AGC) 210d, is used to condition the first electric signal S1 so that a second electric signal S2 is output after the first electric signal S1 orderly passing through the buffer 210a, high-pass filter 210b, low-pass filter 210c and an automatic gain controller (AGC) 210d. The converter 220, which is preferably a analog-to-digital converter (ADC) and electrically connected to the automatic gain controller (AGC) 210d for receiving the second electric signal S2 therefrom, is used to convert the second electric signal S2 into a first digital signal D and transmit it to the successive microprocessor 230. The microprocessor 230, which is electrically connected to precedent converter 220 and successive wireless transmitter 240, is used to process the first digital signal D from the precedent converter 220 and transmit the first digital signal D to the successive wireless transmitter 240. And the wireless transmitter 240 is used to transform the first digital signal D from the precedent microprocessor 230 into a second digital signal D' and transmit the second digital signal D' to the feedback platform 300.

Figure 3A:
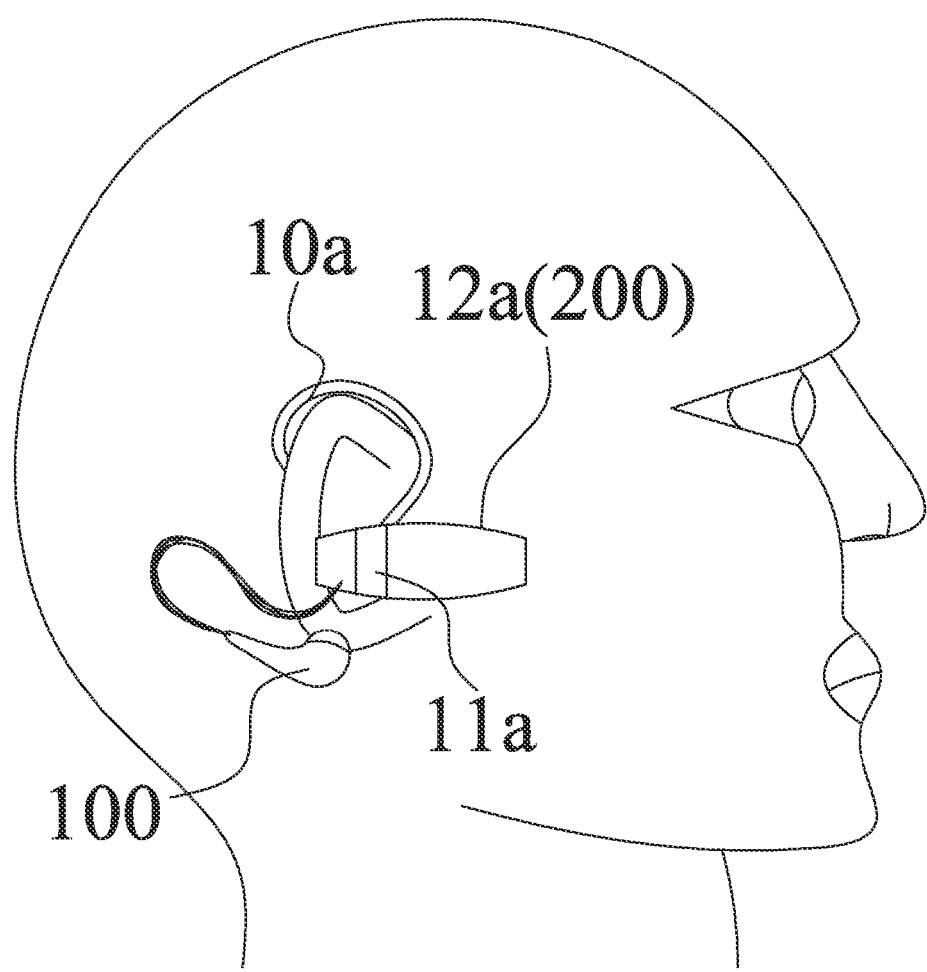
FIGS. 3A and 3B are illustrative views of different earphone structures in a preferred exemplary embodiment of the present invention.
Figure 3B:
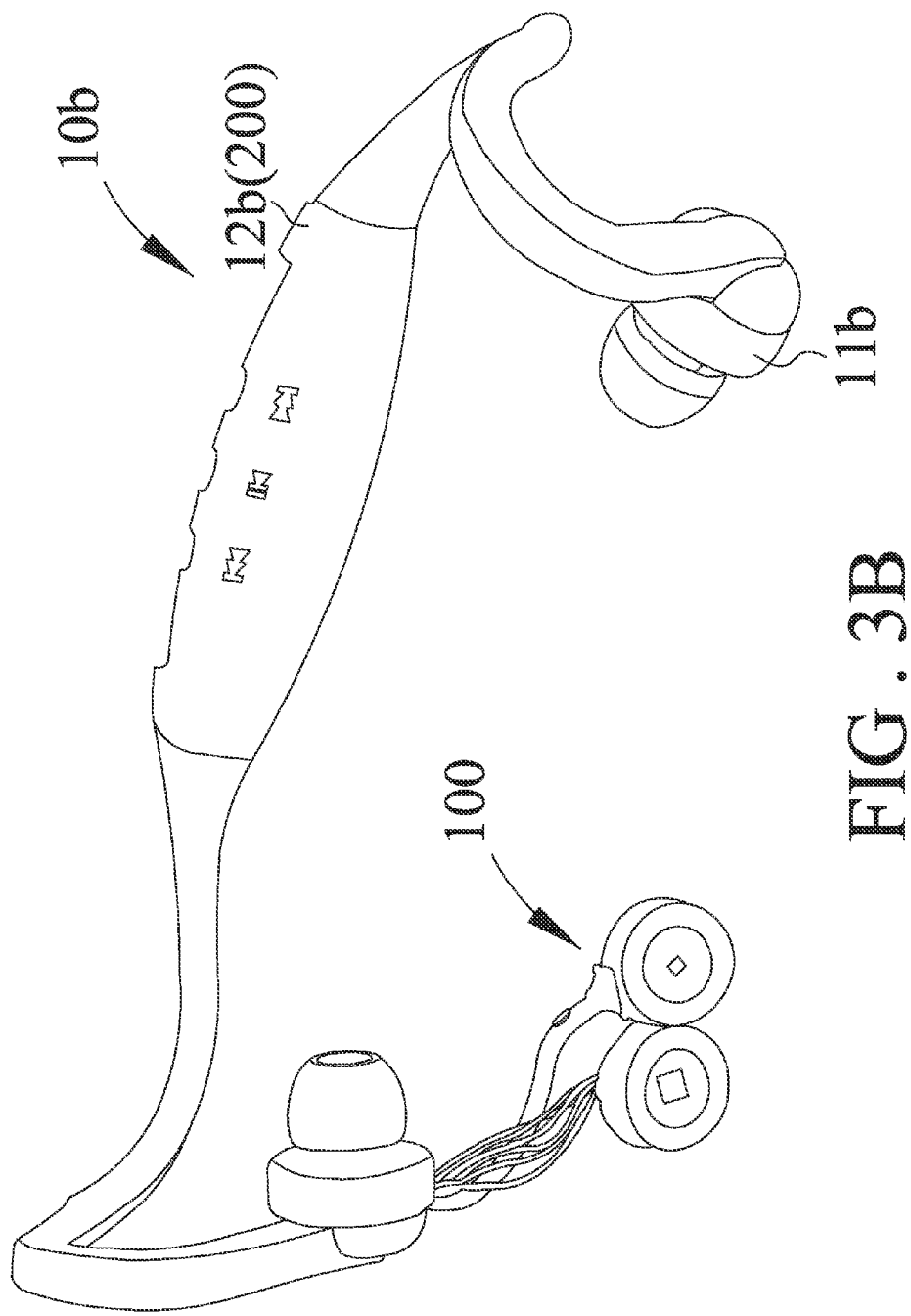

In an exemplary embodiment, the signal processing module 200 is a system-on-a-chip (SoC) of surface mounted device (SMD) to reduce size of hardware circuits contained therein. Please refer to FIGS. 3A and 3B, which are illustrative views of different earphone structures in a preferred exemplary embodiment of the present invention. The earphone 10a is preferably a Bluetooth earphone in FIG. 3A, while the earphone 10b is preferably a neckband type or back-wear type sports headphone in FIG. 3B.

The sensor module 100 is adjacently disposed in a sound source 11a, 11b so that the first magnetic unit 110 and second magnetic unit 120 of the sensor module 100 can easily fix on the earlobe of the examinee user U by mutual magnetic attraction thereof while the signal processing module 200 is preferably disposed in a earpiece 12a, 12b when in practical usage.

Figure 4:
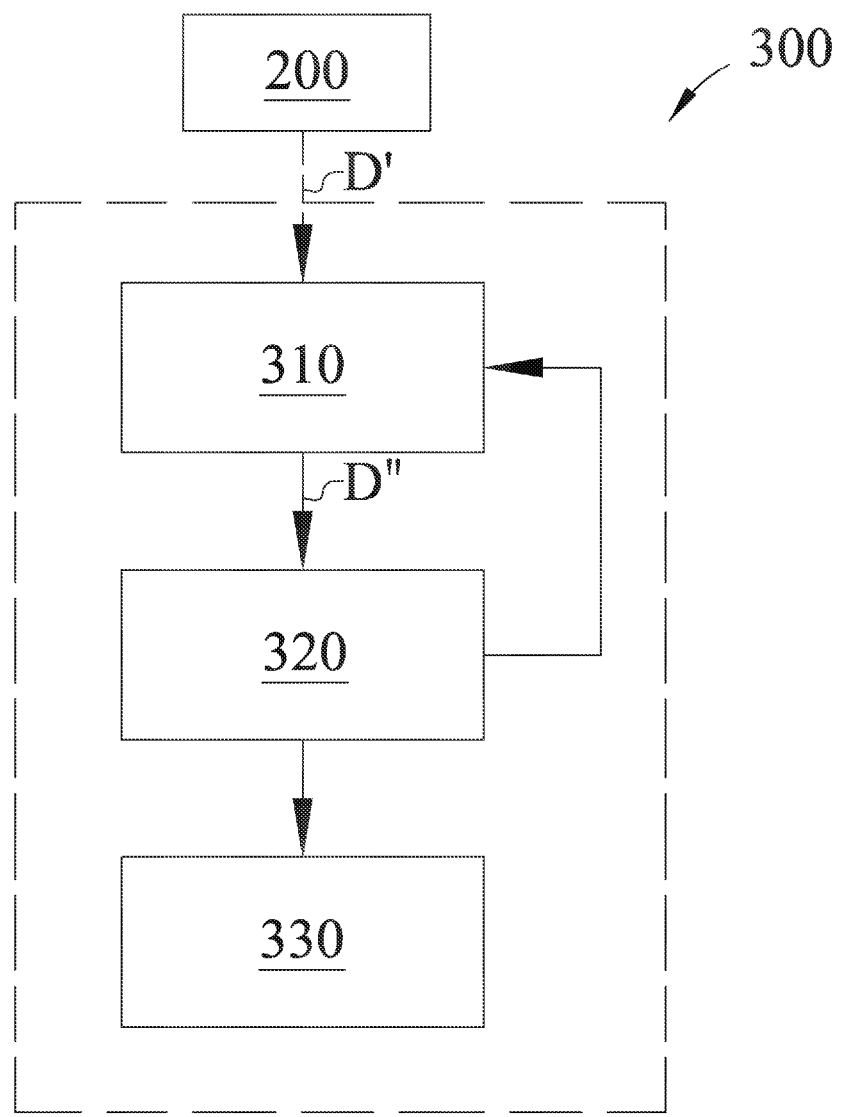
FIG. 4 is a schematic block diagram showing signal transmission between the signal processing, module and feedback platform in a preferred exemplary embodiment of the present invention.

Please refer to FIGS. 2 and 4. The feedback platform 300, which is preferably a mobile telecommunication device such as smart phone, notebook, tablet personal computers (tablet PC) or the like, includes a wireless receiver 310, a real-time process unit 320 and an alarm unit 330. The wireless receiver 310 is used to receive the second digital signal D' from the wireless transmitter 240 and to transform it into a third digital signal D". The real-time process unit 320, which is electrically connected to the wireless receiver 310 for receiving the third digital signal D" therefrom, is used for processing the third digital signal D" to generate physiological parameters such as heart rate value (HR), blood oxygenation concentration value and the like.

A gravity sensing element (G-sensor) 122 is further embedded in the sensor module 100. The G-sensor 122 is electrically connected to the signal processing module 200. If the sensor module 100 is shaken or detects any acceleration or deceleration, the G-sensor 122 generates a third electric signal S3, which will be transmitted to the feedback platform 300 and transmitted to the supervisory platform 400 orderly via the converter 220, microprocessor 230 and wireless transmitter 240. The third electric signal S3 in the feedback platform 300 is served to assist various operations to produce precise physiological signal in reducing motion artifact while the third electric signal S3 in the supervisory platform 400 is functioned to provide auxiliary data to the medical personnel to have better interpretation and judgment for the postural and moving status of the examinee user U so that any abnormality in physiological parameter incurred by the postural and moving anomaly of the examinee user U can be timely obtained.

Figure 5:
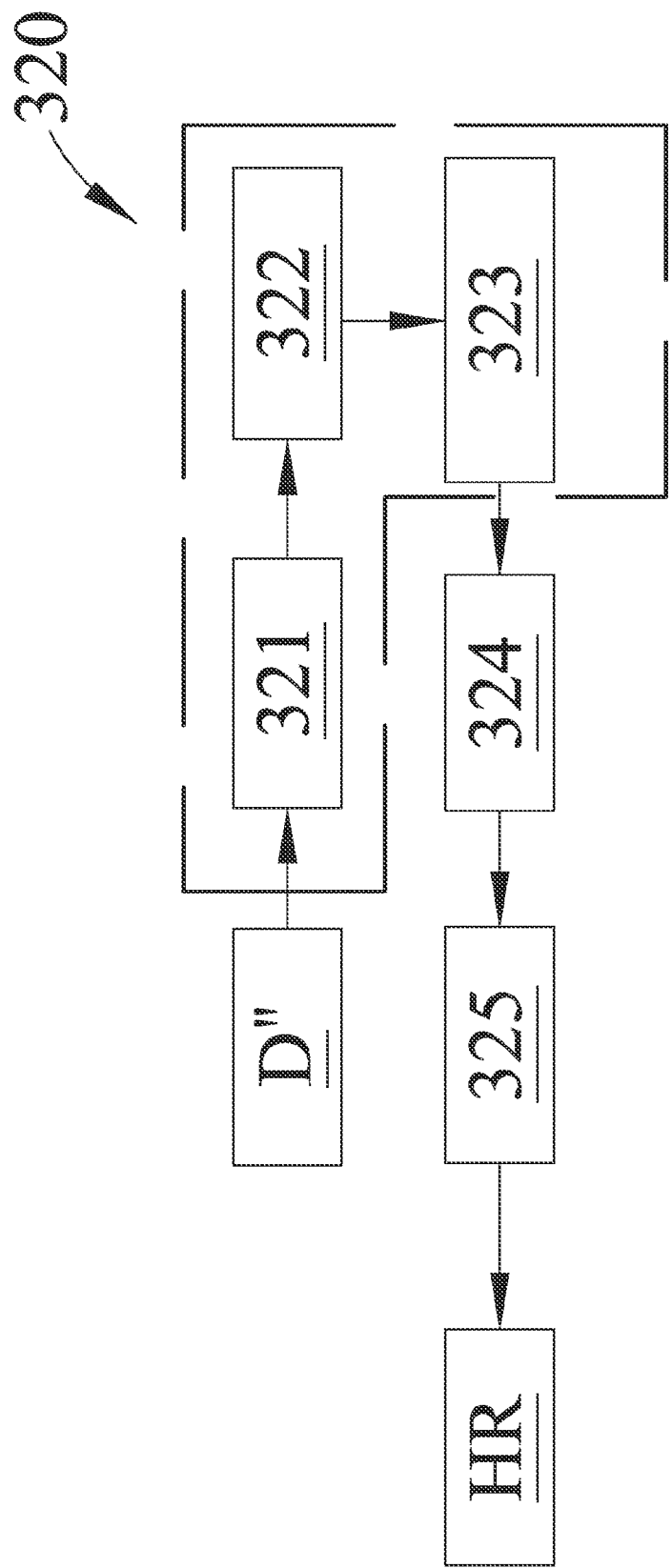
FIG. 5 is a schematic block diagram showing signal transmission between the real-time process unit and outside related components in a preferred exemplary embodiment of the present invention.

Please refer to FIG. 5, which is a schematic block diagram showing signal transmission between the real-time process unit and outside related components in a preferred exemplary embodiment of the present invention. Taking heart rate value (HR) as a typical physiological signal, the processing steps for the algorithm of the real-time process unit 320 are described as below. The real-time process unit 320 includes a bandpass filter 321, a squaring amplifier 322, a differential amplifier 323, a wave peak detector 324 and a heart rate counter 325. The bandpass filter 321 is used to remove noise from the third digital signal D" and transmit the third digital signal D" to successive squaring amplifier 322. The squaring amplifier 322 is used to square and amplify the noise-free third digital signal D" after the noise is removed from precedent bandpass filter 321, and transmit the noise-free third digital signal D" to successive differential amplifier 323. The differential amplifier 323 is used to differentiate the amplified third digital signal D" for extracting a continual waveform with related slope values from precedent squaring amplifier 322, and transmit the amplified third digital signal D" to successive wave peak detector 324. The wave peak detector 324 is used to obtain a new continual waveform with corresponding wave peak values in complex number in accordance with the continual waveform with related slope values from precedent differential amplifier 323, and transmit it to successive heart rate counter 325. And the heart rate counter 325 is used to obtain a heart rate value (HR) in accordance with a time interval between two adjacent wave peaks in accordance with the continual waveform with wave peak values in complex number front precedent wave peak detector 324.

Please refer to FIG. 4, which is a schematic block diagram showing signal transmission between the signal processing module and feedback platform in an exemplary embodiment of the present invention. The alarm unit 330, which is electrically connected to the real-time process unit 320 for receiving physiological parameters therefrom, is used to trigger an alarm if any received physiological parameter such as heart rate value (HR), blood oxygenation concentration value or the like exceeds a referential threshold range, which can be preset with the alarm unit 330. The alarm includes a sound alerting effect, a vibration alerting effect or a visual alerting message prompt on the display.

Figure 6:
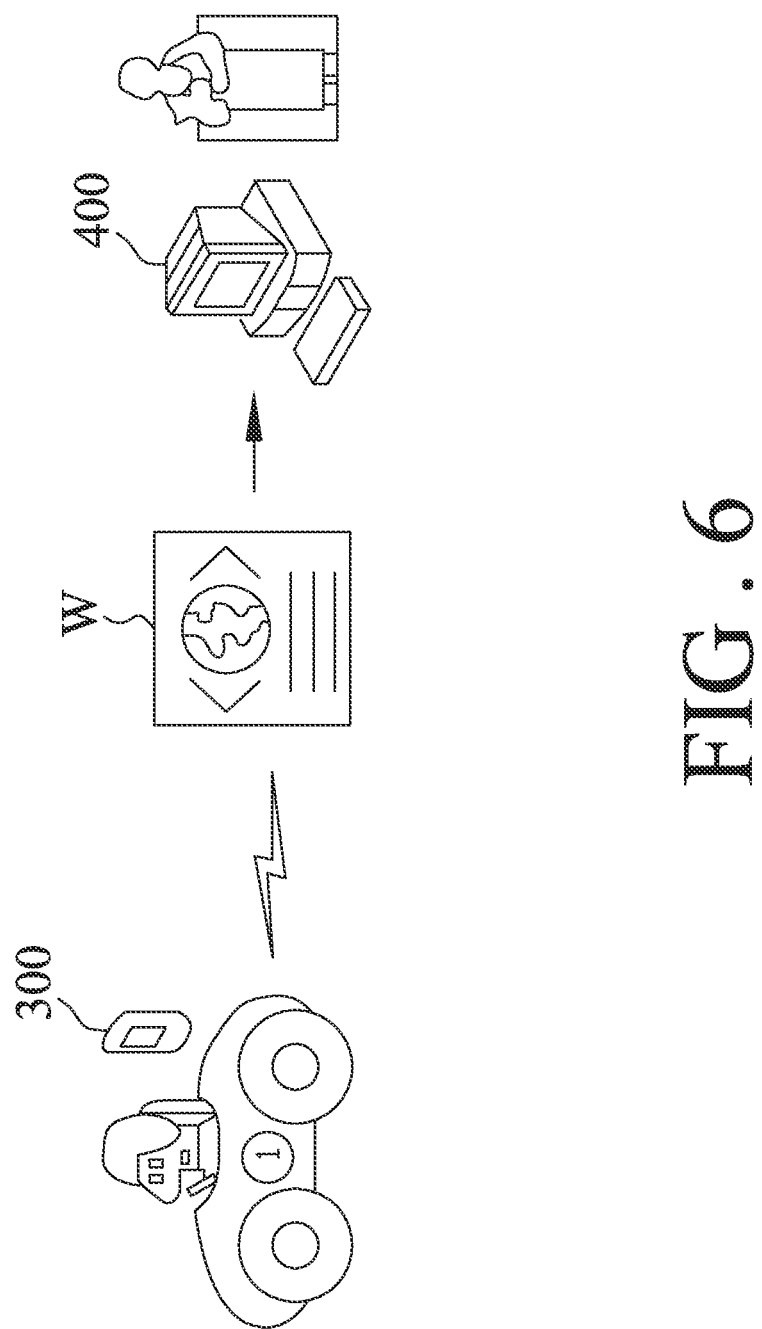
FIG. 6 is a schematic block diagram for a real-time physiological signal measurement and feedback system in another preferred exemplary embodiment of the present invention.

Please refer to FIG. 6, which is a schematic block diagram for a real-time physiological signal measurement and feedback system in another exemplary embodiment of the present invention. The system comprises the sensor module 100, the signal processing module 200, the feedback platform 300 including a mobile communication device and an independent supervisory platform 400 including a medical center. The sensor module 100 is used for perceiving and acquiring external signal. The signal processing module 200 is used to extract, condition and process signals from the sensor module 100. The feedback platform 300, which further includes a global positioning system (GPS) used for getting a position of the examinee user U, is used to trigger the alarm if any abnormality of received physiological parameter is detected so that the alarm of the sound alerting effect or the vibration alerting effect in a mobile communication device is trigged to alert the examinee user U. passersby or emergency contact people. Moreover, the feedback platform 300 serves to transmit both signals of physiological parameters and position of the examinee user U to the supervisory platform 400. The medical personnel in the medical center of the supervisory platform 400 can judge how to handle it on the basis of both signals of physiological parameters and position of the examinee user U from the feedback platform 300.

Besides, the feedback platform 300 can be integrated with a vehicle driving recording system, which can record a driving video comprising an image inside and outside the vehicle, wherein the image inside the vehicle relates to the facial expression and body movement of the vehicle driver while the image outside the vehicle relates to surrounding status during vehicle running on the road. In this case of embodiment, the feedback platform 300 serves to transmit all signals of physiological parameters and position of the examinee user U as well as the driving video to the supervisory platform 400 either via mobile communication network or valid means available; and the medical personnel in the medical center of the supervisory platform 400 can judge what medical issue is, who are involved as well as where and when it does happen on the basis of all signals from the feedback platform 300, then decide how to handle it.

To conclude all disclosure heretofore, the real exemplary embodiment of the present invention mentioned above has following advantages;

1. By means of two magnetic units securely fixing on the earlobe of the examinee user, the sensor module of the present invention can significantly reduce noises.

2. By means of transmitting relevant signals to the feedback platform and supervisory platform, the examinee user and medical personnel can understand related physiological parameters and position at beginning best favorable time.

3. The feedback platform is used as a multi-function driving recorder, also called a car black box, to record the image data and the physiological parameter for identifying the person who is liable for traffic accident.

The foregoing description of the preferred embodiment of the invention has been presented for purposes of illustration and description. It is not intended to be exhaustive or to limit the invention to the precise form or to exemplary embodiments disclosed. Accordingly, the foregoing, description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like is not necessary limited the claim scope to a specific embodiment, and the reference to particularly preferred exemplary embodiments of the invention does not imply a limitation on the invention, and no such limitation is to be inferred. The invention is limited only by the spirit and scope of the appended claims. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning, of the claims. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A real-time physiological signal measurement and feedback system, comprising:
   a sensor module, adapted to being held on a body part of an user, comprising a first magnetic ring surrounding and integrated with a light emitting diode (LED), and a second magnetic ring surrounding and integrated with a photo-detector, such that the light emitting diode is aligned with the photo-detector and illuminates a light beam passing through the body part of the user for being received by the photo-detector thereby a first electric signal is generated by the photo-detector, when the first magnetic ring and the second magnetic ring magnetically attract mutually and sandwich the body part of the user therebetween;
   a signal processing module, electrically connected to the sensor module for receiving the first electric signal therefrom, for processing the first electric signal to generate a second electric signal and convert the second electric signal into a digital signal; and
   a feedback platform for receiving and processing the digital signal received from the signal processing module to generate a physiological parameter, and trigger an alarm according to the physiological parameter.

2. The real-time physiological signal measurement and feedback system of claim 1, wherein the sensor module comprises a gravity sensing element such that the gravity sensing element generates a third electric signal if the sensor module is shaken.

3. The real-time physiological signal measurement and feedback system of claim 1, wherein the signal processing module is a system-on-a-chip (SoC), and comprises an operation amplifier, a converter and a wireless 25 transmitter, wherein the operation amplifier is used for processing the first electric signal to output a second electric signal; the converter is electrically connected to the operation amplifier for receiving the second electric signal therefrom and converting the second electric signal into the digital signal; and the wireless transmitter is electrically connected to the 30 converter for sending the digital signal to the signal processing module.

4. The real-time physiological signal measurement and feedback system of claim 1, wherein the feedback platform comprises a wireless receiver, a real-time process unit and an alarm unit, wherein the wireless receiver is used to receive the digital signal; the real-time process unit is signally connected to the wireless receiver for generating the physiological parameter according to the digital signal; and the alarm unit is electrically connected to the real-time process unit for triggering the alarm.

5. The real-time physiological signal measurement and feedback system of claim 4, wherein the real-time process unit comprises a bandpass filter, a squaring amplifier and a differential amplifier, wherein the bandpass filter is used to remove a noise from the digital signal; the squaring amplifier is used to amplify the digital signal after the noise is removed from precedent bandpass filter; and the differential amplifier is used to differentiate the digital signal amplified by the squaring amplifier for extracting a slope value.

6. The real-time physiological signal measurement and feedback system of claim 4, wherein the real-time process unit comprises a wave peak detector and a heart rate counter, wherein the wave peak detector is used to obtain a plurality of wave peak values in accordance with the slope value; and the heart rate counter is used to obtain a heart rate value (HR) in accordance with a time interval between two wave peak values.

7. The real-time physiological signal measurement and feedback system of claim 1, wherein the alarm unit comprises a referential threshold range for triggering the alarm if the physiological parameter exceeds the referential threshold range.

8. The real-time physiological signal measurement and feedback system of claim 1, wherein the alarm is a sound alerting effect, a vibration alerting effect or a visual alerting message prompt.

9. The real-time physiological signal measurement and feedback system of claim 1, wherein the feedback platform comprises a mobile communication device and is signally connected to a supervisory platform comprising a medical center.

10. The real-time physiological signal measurement and feedback system of claim 9, wherein the feedback platform comprises a positioning system and a vehicle driving recording system, wherein the positioning system is used for getting a position of the user; the vehicle driving recording system records a driving video comprising an image inside and outside the vehicle; and the feedback platform is used to transmit the physiological parameter and the position of the user as well as the driving video to the supervisory platform.

11. The real-time physiological signal measurement and feedback system of claim 1, wherein the feedback platform is a multi-function driving recorder for generating an image data and recording the image data and the physiological parameter.

* * * * *